United States Patent [19]

Gallagher, deceased et al.

[11] Patent Number: 5,334,295

[45] Date of Patent: Aug. 2, 1994

[54] MICRO FUEL-CELL OXYGEN GAS SENSOR

[75] Inventors: John P. Gallagher, deceased, late of Jupiter, Fla., by Janice M. Gallagher; Robert J. Masi, Littleton, Mass.

[73] Assignee: Delta F. Corporation, Woburn, Mass.

[21] Appl. No.: 58,776

[22] Filed: May 3, 1993

Related U.S. Application Data

[62] Division of Ser. No. 864,491, Apr. 7, 1992, Pat. No. 5,256,273.

[51] Int. Cl.$^5$ ............................................ G01N 27/26
[52] U.S. Cl. .......................... 204/153.16; 204/153.17; 204/153.22; 204/412; 204/415; 204/431; 204/432; 204/258; 204/265; 204/277; 204/278
[58] Field of Search ...................... 204/153.16, 153.17, 204/153.22, 412, 415, 416, 418, 419, 431, 432, 258, 265, 266, 277, 278

[56] References Cited

U.S. PATENT DOCUMENTS 3,929,587 12/1975 Gallagher ........................... 204/432
4,960,497 10/1990 Gallagher, deceased ..... 204/153.16

Primary Examiner—John Niebling
Assistant Examiner—Bruce F. Bell
Attorney, Agent, or Firm—Samuels, Gauthier & Stevens

[57] ABSTRACT

An oxygen sensor for measuring oxygen in the ppb range. The sensor comprises an electrochemical cell. The oxygen is metered to the cathode based on gaseous phase diffusion to provide a measurement proportional to volumetric concentration. Hydrogen is metered to the anode in an amount in excess of the oxygen being reduced at the cathode. A current is generated which is linear to the volumetric concentration of the oxygen in the sample gas. The concentration of the oxygen is measured based on the current generated.

24 Claims, 1 Drawing Sheet

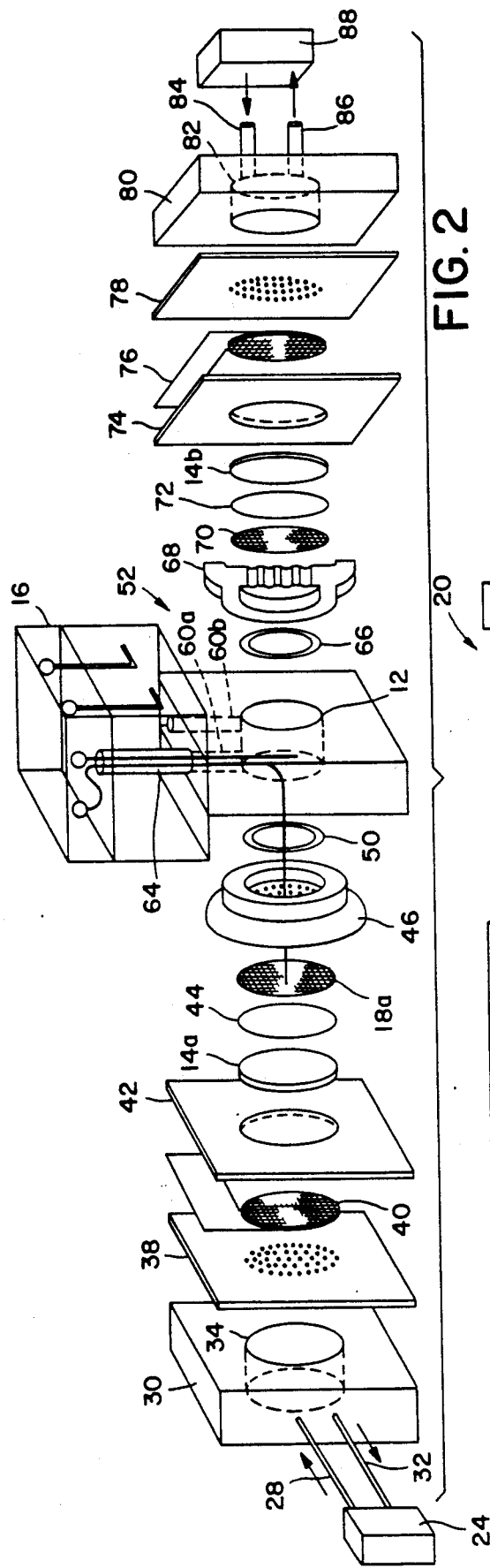
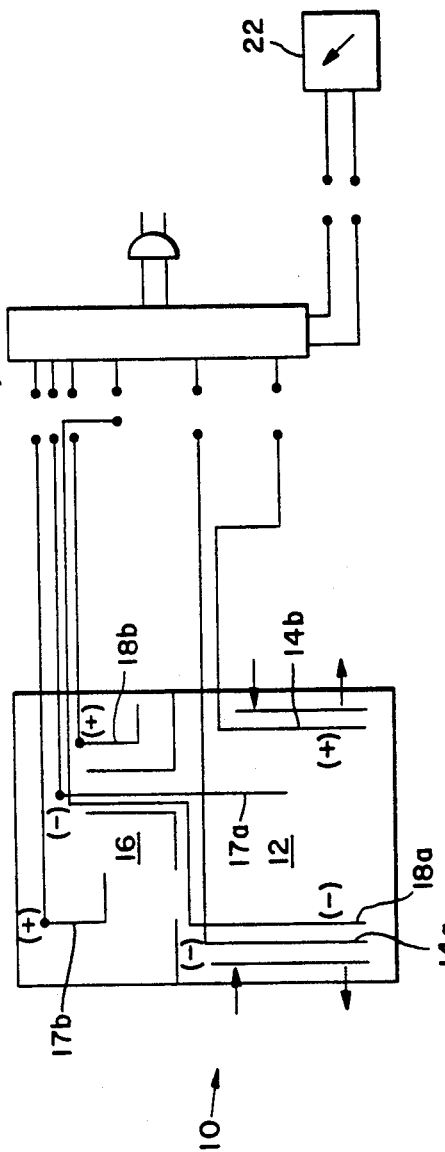

MICRO FUEL-CELL OXYGEN GAS SENSOR

This is a divisional of copending application Ser. No. 07/864,491 filed on Apr. 7, 1992, now U.S. Pat. No. 5,256,273.

BACKGROUND AND BRIEF SUMMARY OF THE INVENTION

An electrochemical cell, in its simplest terms, consists of an anode (the oxidizing electrode), a cathode (the reducing electrode) and an electrolyte. In order for the electrochemical cell to function, the electrolyte must be compatible with the mechanisms of oxidation and reduction at the electrodes. As well, it must provide a conductive path for the transport of ionic species between the electrodes.

The electrochemical cell concept is broadly applied in industrial and scientific operations. Electrolytic cells are used in electroplating, water purification, and the production of high purity gases and metals while electrochemical cells, such as batteries and fuel cells provide a convenient means of energy storage and generation.

Also, due to their very high level of sensitivity, electrochemical cells are used for measurement in a variety of analytical procedures and many laboratory and process control instruments depend on the electrochemical cell as the sensing element for their function.

U.S. Pat. No. 4,960,497 discloses a system wherein an electrolytic cell measures oxygen in the ppb range. In this system, the dissolved oxygen in the electrolyte is removed to allow for an accurate reading of the oxygen concentration in a gas sample. However, in this system, when measuring in the 0–100 ppb range, it was found that in some instances the signal-to-noise ratio was not high enough to provide a consistently accurate reading.

There are other electrochemical systems currently available which measure oxygen in the 0–100 ppb range. In these systems, the anode, typically lead or cadmium, functions as a consumable half cell. A drawback inherent in these systems is that because the anode is consumed, its properties or characteristics change over time and this can affect the accuracy of the measurements, particularly in the ppb range. This drawback is typical of the consumable (battery) type electrochemical oxygen sensor.

The present invention is directed to an electrochemical system and a method for measuring an analyte, i.e. oxygen, hydrogen, ammonia and hydrazine in the ppb range. Broadly the system functions as a hydrogen-oxygen alkaline fuel cell configured to generate a current which is linear to the rate at which the analyte is either reduced at a cathode., i.e. oxygen or oxidized at the anode, i.e. hydrogen, ammonia, hydrazine. The inventive system differs from prior art fuel cells in that prior art fuel cells are designed or configured to optimize the output of electrical energy and are not designed to function as an analyte sensor, particularly in the ppb range. The present invention differs from the prior art sensor ppb oxygen systems described above because in the inventive system the anode is non-depleting or non-consumable. In this inventive system, no chemical changes take place within the sensor, thus allowing the oxygen measurement to remain stable over time.

In the preferred embodiment, the invention comprises an electrochemical cell. A gaseous stream containing the oxygen to be measured contacts a cathode catalytically optimized for oxygen. The oxygen is reduced forming hydroxyl ions. Simultaneously, a stream of hydrogen contacts a non-depleting anode. The hydrogen is oxidized (in the presence of the hydroxyl ions), and collectively these reactions generate a current which is proportional to the rate at which oxygen is reduced at the cathode. The current measured corresponds exactly to the changing concentration of oxygen in the gaseous stream.

One advantage of this invention is that the system is a relatively clean system, the redox byproduct being water as opposed to lead oxide (lead anode) or cadmium hydroxide (cadmium anode). In this system, the water byproduct harmlessly evaporates, while the lead oxide and cadmium hydroxide byproducts build up in the sensor cell and act as inhibitors to the electrochemical reactions.

Distinct advantages over the previous ppb oxygen sensor system disclosed in U.S. Pat. No. 4,960,497 include higher oxygen sensitivity, lower background offset, less offset drift, improved linear response, improved speed of response and reduced temperature sensitivity.

BRIEF DESCRIPTION OF THE DRAWINGS

FIG. 1 is a functional block diagram of an embodiment of the invention; and

FIG. 2 is an exploded perspective view of an embodiment of the invention.

DESCRIPTION OF THE PREFERRED EMBODIMENT(S)

Referring to FIG. 1, a block diagram of an electrochemical system 10, of the preferred embodiment of the invention is shown and includes an electrochemical cell cavity 12 having two sensing electrodes 14a and 14b and two additional electrodes 18a and 17a disposed therein. A reservoir 16 is in fluid flow communication with the cell cavity 12 and includes an electrode 18b and an electrode 17b. The load for the sensing electrodes 14a and 14b is provided by a DC circuit and power conditioner 20. The electrolyte in cell cavity 12 with the electrodes 14a and 14b completes the electrolytic circuit. The power conditioner 20 applies a constant potential across electrodes 18a and 18b and the electrolyte common to the cell cavity 12 and reservoir 16 by a separate DC circuit (not shown). The power conditioner 20 also provides a constant current between electrodes 17a and 17b and the electrolyte common to the cell cavity 12 and reservoir 16 via a third separate DC circuit (not shown). Although also not shown, the power conditioner will include the appropriate resistors, amplifiers, etc. in order to control specifically the circuit condition required by each of the three independent sets of electrodes. A meter 22 communicates with electrodes 14a and 14b via the power conditioner 20 to provide a direct reading corresponding to the electroreduction of the component to be analyzed.

Referring to FIG. 2, the cell cavity 12 and reservoir 16 are shown in greater detail. A gaseous stream containing the analyte to be analyzed flows from a source 24 through an inlet 28 and into an inlet plate 30. The inlet plate 30 includes a cavity-like recess 34 through which the gaseous stream flows. An apertured diffuser plate 38 meters the diffusion of oxygen in the sample stream to the electrode 14a. A current collector 40 is sandwiched between the diffuser plate 38 and an electrode retainer plate 42 having an aperture therein. The electrode 14a is received in the aperture. A non-conductive permeable separator 44 is interposed between the electrode 14a and a platinum screen electrode 18a. An electrolyte plate 46 having flow passages therein abuts the electrode 18a on one side and on the other side receives an O-ring 50.

A housing 52 generally comprises the lower cell cavity housing 12 and the upper reservoir 16. Conduits 60a and 60b are formed in the cell cavity housing 12 and are received in the bottom of the reservoir 16. A sleeve 64 in the reservoir is placed over the conduit 60a to isolate electrodes 17a and 18a from electrodes 17b and 18b via conduit 60b. Both the connecting wire for electrode 18a and electrode 17a pass through the sleeve 64. The electrodes 17b and 18b are secured in any suitable manner within the reservoir 16. The electrolyte in the cell cavity 12 and the reservoir 16 are in fluid flow communication with one another only via the conduit 60b.

On the other side of the housing 52 are an O-ring 66, an electrolyte plate 68 having flow passages therein, a stainless steel screen 70, a non-conductive permeable separator 72, such as an asbestos membrane, the electrode 14b, an electrode retainer plate 74, a current collector 76, and a gas diffuser plate 78. An inlet plate 80 includes a cavity-like recess, an inlet 84 and an outlet 86 through which a minute amount of hydrogen flows. The diffuser plate 78 meters the hydrogen diffusion to the electrode 14b.

The electrode 14a (which functions as a cathode) is generally any semi-permeable electrode catalytically specific to oxygen. A non-specific cathode may be used as long as the rate of oxygen reduction at the cathode is proportional to the oxygen diffusion rate through the diffuser plate 38. The electrode 14b is a semi-permeable electrode catalytically specific to hydrogen.

The electrode 17a is preferably a metal such as nickel and the corresponding electrode 17b is platinum.

The electrode 18a, specifically a barrier electrode, is preferably a platinum wire mesh. The corresponding electrode 18b is preferably a platinum rod.

OPERATION OF THE INVENTION

In the operation of the invention, an aqueous electrolyte (such as a solution of 1M potassium hydroxide) is introduced into the reservoir and cell cavity. A first electrolytic path is established between electrodes 14a and 14b in the cell cavity 12, a second electrolytic path is established between the electrodes 17a and 17b and a third electrolytic path is established between the electrodes 18a and 18b. The second and third electrolytic paths use the electrolyte common to the cell cavity 12 and the reservoir 16. The three pairs of electrodes 14a-14b, 17a-17b, and 18a-18b are connected to the power conditioner 20 through appropriate connectors (not shown). The power conditioner 20 includes an appropriate circuit which provides a small continuous current between electrodes 17a and 17b. The power conditioner 20 includes an appropriate measurement circuit to sense the current produced electrochemically by electrodes 14a and 14b. The power conditioner 20 provides a 1.5 VDC potential which is placed across electrodes 18a and 18b.

A gaseous sample stream 24 containing some finite concentration of oxygen flows through inlet plate 30. A flow rate of between 0.5 to 3 scfh is preferred. The gas may be at a temperature of between 32°-120° F. and at a pressure of about 1 psi gauge. At the same time, a stream of hydrogen from a source 88 flows through inlet plate 80. The required flow rate here is approximately 10 scch. A negligible amount of this hydrogen is actually consumed in the electrochemical reaction and the remaining hydrogen gas is safely vented away via the outlet 86. This low level hydrogen supply can easily be generated by collecting evolved hydrogen from a controlled water electrolysis.

Oxygen in the sample stream diffuses through the diffuser plate 38 and is electrochemically reduced at electrode 14a. This electrode 14a, which functions as a cathode, is preferably a metal catalyzed carbon-Teflon electrode. Hydrogen in the source supply diffuses through the diffuser plate 78 and is electrochemically oxidized at electrode 14b. This electrode 14b, which functions as an anode, may be any semi-permeable electrode containing a catalytically active metal for the oxidation of hydrogen, preferably platinum.

In this embodiment, oxygen is electrochemically reduced at electrode 14a producing hydroxyl ions $OH^-$. The hydroxyl ions migrate across the cell cavity 12 to electrode 14b where they complete the ionic circuit and facilitate the oxidation of hydrogen to form water.

The sensing device 10 produces current in exact proportion with the rate at which oxygen in the sample gas diffuses to electrode 14a. The current produced (i.e. the oxygen diffusion rate) is exactly linear with the changing oxygen concentration when the sensor is operated in the current limiting region. The current produced by the sensor when oxygen is present in the gaseous sample 24 is measured by the power conditioner 20 and displayed by the meter 22. For example, with a 7 ppm oxygen concentration in the gas sample 24, the diffusion rate of oxygen to electrode 14a is approximately 4.7 E-3 cc/hr and produces a current of 21 micro-amps in the cell. At this current, the sensor will consume 9.4 E-3 cc/hr of hydrogen. When the oxygen concentration in gas sample 24 is reduced to 70 ppb the cell current is linearly reduced to 210 nano-amps, thus providing an ideally linear response to changing oxygen concentration.

Electrodes 17a and 17b perform a separate function which is integral to the operation of the sensing device 10. They provide a mechanism to remove and/or entrap trace ionic impurities in the electrolytic solution. The introduction of such trace impurities into the electrolyte may come from one or all of three possible sources: they are present in the original electrolytic solution; secondly, they are introduced into the electrolytic solution as a result of separate chemical reactions between the materials of construction of the sensor (including the electrodes) and the electrolyte; and lastly, they enter as contaminants, e.g. acid gases, from the gaseous sample streams.

The elimination of, or protection against, these trace ionic impurities is important in the monitoring of trace (<100 ppb) oxygen streams. With cell current continually reducing, as when measuring lower and lower oxygen concentrations, trace ionic impurities become more problematic for stable sensing. These impurities may be strongly adsorbed at the active sites and thus lower the effective surface area for oxygen reduction. Trace ionic impurities also influence the adsorption of reactants or intermediates which may alter the electrochemical sensitivity to oxygen. The presence of electrodes 17a and 17b at an applied potential and fixed current has a scavenging effect on trace ionic impurities in solution, thus protecting the oxygen sensing electrodes 14a and 14b and providing a long-term stable measurement. This function is disclosed in U.S. Pat. No. 3,929,587 which is hereby incorporated by reference in its entirety into this disclosure.

Electrodes 18a and 18b perform a still separate function which is integral to the operation of the sensing device 10. They provide a mechanism which removes the dissolved oxygen from the electrolyte retained in the cell cavity 12. This is important because the presence of even trace amounts of dissolved oxygen will produce current and impede the accurate analysis of ppb levels of oxygen in the gaseous sample stream. The power conditioner 20 provides a potential of approximately 1.5 VDC between electrodes 18a and 18b. In this potential range, hydrogen is evolved on the electrode 18a. The details of this function are disclosed in U.S. Pat. No. 4,960,497 which is hereby incorporated by reference in its entirety into this disclosure.

The foregoing description has been limited to a specific embodiment of the invention. It will be apparent, however, that variations and modifications can be made to the invention, with the attainment of some or all of the advantages of the invention. Therefore, it is the object of the appended claims to cover all such variations and modifications as come within the true spirit and scope of the invention.

Having described my invention, what I now claim is:

1. A method for measuring the amount of oxygen in a gas which includes:
   establishing in an electrolyte an electrolytic path between sensing electrodes comprising a cathode and an anode;
   flow the gas to the cathode;
   metering the oxygen to the cathode based on gaseous phase diffusion to provide a measurement proportional to volummetric concentration;
   reducing the oxygen at the cathode to form hydroxyl ions;
   placing hydrogen in contacting relationship with the anode; and
   oxidizing the hydrogen at the anode to form water and to establish a current which current is linear to the volummetric concentration of the oxygen reduced at the cathode; and
   measuring the oxygen reduced.

2. The method of claim 1 which includes:
   flowing the gas into a cavity; and
   metering the gas from the cavity through a diffusion plate to the cathode.

3. The method of claim 2 which includes:
   flowing the gas into the cavity at a rate of 0.5 and 3.0 scfh.

4. The method of claim 2 where the gas is at a temperature between about 32° and 125° F.

5. The method of claim 2 where the gas is at a pressure of about 1.0 psig.

6. The method of claim 1 wherein the electrolyte is aqueous 0.1-10M KOH.

7. The method of claim 1 wherein the cathode is a catalyzed carbon-tetrafluorethylene electrode specific to oxygen reduction.

8. The method of claim 1 which includes:
   flowing hydrogen to a cavity; and
   metering the hydrogen from the cavity through a diffusion plate to the anode.

9. The method of claim 8 which includes:
   flowing the hydrogen into the cavity at a rate of 10 to 25 scch.

10. The method of claim 8 wherein the hydrogen concentration delivered to the cavity is typically about 100% by volume.

11. The method of claim 1 wherein the anode is a platinum catalyzed carbon-tetrafluoroethylene electrode specific to hydrogen oxidation.

12. The method of claim 1 wherein the electrolytic path between the cathode and the anode is a first electrolytic path and which includes:
    providing a first barrier electrode and a second electrode, the barrier electrode interposed between the cathode and the electrolyte, the first and second electrodes completing a second electrolytic path, the function of which is independent of the function of the first electrolytic path; and
    applying a voltage across the first and second electrodes to activate the barrier electrode such that unwanted components in the electrolyte are electrolytically inhibited from diffusing to the cathode.

13. The method of claim 12 which includes:
    providing a reservoir of electrolyte in communication with the electrolyte of the cell and wherein the second electrode is disposed in the reservoir, the electrolytes of the cell and the reservoir being in fluid flow communication.

14. The method of claim 12 which includes:
    polarizing the first barrier electrode to evolve hydrogen on said first barrier electrode while generating oxygen at the second electrode.

15. The method of claim 14 wherein the oxygen generated at the second electrode effervesces from the reservoir.

16. The method of claim 14 where the current between the barrier electrode and the second electrode is equivalent to the equilibrium concentration of $O_2$ available at the barrier electrode.

17. The method of claims 1 or 12 wherein the electrolytic path between the cathode and the anode is a first electrolytic path and which includes:
    providing a reservoir of electrolyte in communication with the electrolyte and providing a third pair of electrodes, one of said electrodes disposed in the reservoir of electrolyte and the other of said electrodes disposed in the electrolyte, which pair of electrodes provides a third electrolytic path, the function of which path is independent of the function of the first electrolytic path;
    generating a current between the third pair of electrodes resulting in a pH gradient between the electrolyte of the reservoir and the electrolyte to provide for the migration of unwanted ionic species from the electrolyte to the reservoir, which unwanted species do not directly affect reactions at the cathode; and
    restricting the back diffusion of the unwanted ionic species from the reservoir into the cell, whereby the unwanted ionic species remain segregated from the electrolyte.

18. The method of claim 17 which includes:
    establishing a zone of hydroxyl ions in the electrolyte of the reservoir of a different concentration than the hydroxyl ions in the electrolyte.

19. The method of claim 17 which includes:
    emitting the ionic species from the reservoir by effervescence.

20. The method of claim 17 which includes:
    emitting the ionic species by direct oxidation at the anode.

21. The method of claim 17 which includes:
scavenging the ionic species via electrode surface adsorption.

22. A method for measuring the amount of an analyte in a gas which includes:
establishing in an electrolyte an electrolytic path between sensing electrodes;
flowing the gas to a sensor electrode catalytically specific to the analyte;
metering the gas to an electrode catalytically specific to the analyte based on gaseous phase diffusion to provide a measurement proportional to volummetric concentration;
converting the analyte to a non ionic species;
establishing a current in the electrolyte which is linear to the volummetric concentration at which the analyte is converted to a non ionic species in the sample gas;
metering oxygen to the other electrode to form an ionic species, the oxygen maintained in excess relative to the analyte being oxidized; and
measuring the current generated.

23. The method of claim 22 wherein one of the sensing electrodes is an anode and where the analyte is selected from the group consisting essentially of hydrogen, ammonia and hydrazine and which includes:
oxidizing the analyte at the anode.

24. The method of claim 22 wherein one of the sensing electrodes is a cathode and wherein the analyte is oxygen and which includes:
reducing the oxygen at the cathode.

* * * * *